United States Patent
Hatch et al.

(10) Patent No.: US 8,703,058 B1
(45) Date of Patent: Apr. 22, 2014

(54) MICROFLUIDIC DEVICES AND METHODS INCLUDING POROUS POLYMER MONOLITHS

(75) Inventors: Anson V. Hatch, Tracy, CA (US); Gregory J. Sommer, Livermore, CA (US); Anup K. Singh, Danville, CA (US); Ying-Chih Wang, Pleasanton, CA (US); Vinay V. Abhyankar, Dublin, CA (US)

(73) Assignee: Sandia Corporation, Albuquerque, NM (US)

( * ) Notice: Subject to any disclaimer, the term of this patent is extended or adjusted under 35 U.S.C. 154(b) by 596 days.

(21) Appl. No.: 12/556,459

(22) Filed: Sep. 9, 2009

(51) Int. Cl.
*B01J 20/285* (2006.01)
*B01J 20/26* (2006.01)

(52) U.S. Cl.
USPC .............................. 422/69; 422/527; 502/402

(58) Field of Classification Search
USPC ..................... 422/69, 527; 502/402
See application file for complete search history.

(56) References Cited

U.S. PATENT DOCUMENTS

| | | | |
|---|---|---|---|
| 5,866,047 A * | 2/1999 | Nagino et al. | 264/1.27 |
| 6,782,746 B1 | 8/2004 | Hasselbrink | |
| 6,846,399 B2 | 1/2005 | Shepodd | |
| 7,264,723 B2 | 9/2007 | Singh | |
| 2002/0139751 A1 * | 10/2002 | Zhang et al. | 210/656 |
| 2003/0143712 A1 * | 7/2003 | Verdin et al. | 435/196 |
| 2004/0101442 A1 * | 5/2004 | Frechet et al. | 422/99 |

OTHER PUBLICATIONS

Timothy C. Logan; Douglas S. Clark; Timothy B. Stachowiak; Frantisek Svec; Jean M. J. Frechet; "Photopattering Enzymes on Polymer Monoliths in Microfluidic Devices for Steady-State Kinetic Analysis and Spatially Separated Multi-Enzyme Reactions", Analytical Chemistry, 2007, 79, pp. 6592-8598.

J. Lalevee; M. El-Roz; X. Allonas; J. P. Fouassier; "Controlled Photopolymerization Reactions: The Reactivity of New Photoiniferters", Journal of Polymer Science: Part A: Polymer Cheistry, 2007, 45, pp. 2436-2442.

Dieudonne A. Mair; Thomas R. Schwei; Theresa S. Dinio; Frantisek Svec; Jean M. J. Frechet; "Use of photopatterned porous polymer monoliths as passive micromixers to enhance mixing efficiency for on-chip labeling reactions", Lab Chip, 2009, 9, pp. 877-883.

Jana, Krenkova; Frantisek Svec; "Less common applications of monoliths: IV, Recent developments in immoblized enzyme reactors for proteomics and biotechnology", Journal of Separation Science, 2009, 32, pp. 706-718.

Cong Yu; Frantisek Svec; Jean M.J. Frechet; "Towards stationary phases for chomatography on a microchip: Molded porous polymer monoliths prepared in capillaries by photoinitiated in situ polymerization as separation media for electrochromatography", Electrophoresis 2000, 21, pp. 120-127.

Takayuki Otsu; "Iniferter Concept and Living Radical Polymerization", Journal of Polymer Science: Part A: Polymer Chemistry, 2000, 38, pp. 2121-2136.

(Continued)

*Primary Examiner* — Paul Hyun
(74) *Attorney, Agent, or Firm* — Dorsey & Whitney LLP

(57) ABSTRACT

Microfluidic devices and methods including porous polymer monoliths are described. Polymerization techniques may be used to generate porous polymer monoliths having pores defined by a liquid component of a fluid mixture. The fluid mixture may contain iniferters and the resulting porous polymer monolith may include surfaces terminated with iniferter species. Capture molecules may then be grafted to the monolith pores.

22 Claims, 9 Drawing Sheets

(56) References Cited

OTHER PUBLICATIONS

Cong Yu: Mingcheng Xu: Frantisek Svec; Jean M. J. Frechet; "Preparation of Monolithic Polymers with Controlled Porous Properties for Microfluidic Chip Applications Using Photoinitiated Free-Radical Polymerization", Journal of Polymer Science: Part A: 2002, 40, pp. 755-769.

Sarah M. Ngola; Yolanda Fintschenko; Wen-Yee Choi; Timothy J. Shepodd: "Condust-as-Cast Polymer Monoliths as Separation Media for Capillary Electrochromatography", Analytical Chemistry, 2001, 73, pp. 849-856.

Cong Yu; Mark H. Davey; Frantisek Svec; Jean M. J, Frechet; "Monolithic Porous Polymer On-Chip Solid-Phase Extraction and Preconcentration Prepared by Photoinitiated in Situ Polymerization within a Microfluidic Device", Analytical Chemistry, 2001, 73, pp. 5088-5096.

Timothy B. Stachowiak; Thomas Rohr; Emily F. Hilder; Dominic S. Peterson; Mingqiang Yi; Frantisek Svec; Jean M. J, Frechet; "Fabrication of porous polymer monoliths covalently attached to the walls of channels in plastic microdevices", Electrophoresis 2003, 24, pp. 3689-3893.

Thomas Rohr; Emily F. Hilder; John J. Donovan; Frantisek Svec; Jean Frechet; "Photografting and the Control of Surface Chemistry in Three-Dimensional Porous Polymer Monoliths", Macromolecules, 2003, 36, pp. 1677-1684.

Simon Song; Anup K. Singh; Timothy J. Shepodd; Brian J. Kirby; "Microchip Dialysis of Proteins Using in Situ Photopatterned Nanoporous Polymer Membranes", Analytical Chemistry, 2004, 76, pp. 2367-2373.

Jana Krenkova; Frantisek Foret; "Immobiiize microfludic enzymatic reactors", Electrophoresis 2004, 25, pp. 3550-3563.

Helen M. Simms; Christopher M. Brotherton; Brian T Good; Robert H. Davis; Kristi S. Anseth; Christopher N. Bowman; "In situ fabrication of macroporous polymer networks within microfluidic devices by living radical photopolymerication and leaching", Lab Chip, 2005, 5, pp. 151-157.

Robert P. Sebra; Kristyn S. Masters; Christopher N. Bowman; Kristi S. Anseth; "Surface Grafted Antibodies: Controlled Architecture Permits Enhanced Antigen Detection", Langmuir, 2005, 21, pp. 10907-10911.

Timothy B. Stachowiak; Frantisek Svec; Jean M. J. Frechet; "Patternable Protein Resistant Surfaces for Multifunctional Microfluidic Devices via Surface Hydrophilization of Porous Polymer Monoliths Using Photografting", Chemistry of Materials, 2005, 18, pp. 5950-5957.

Wlad Kusnezovv; Yana V. Syagailo; Sven Ruffer; Nina Baudenstiel, Christoph Gauep; Jorg D. Hoheisel; David Wild; Igor Goychuk; "Optimal Design of Microarray Immunoassays to Compensate for Kinetic Limitations", Molecular and Cellular Proteomics 5.9, 2006, pp. 1581-1696.

Robert P. Sebra; Kristyn S. Masters; Charles Y Cheung; Christopher N. Bowman; Kristi S. Anseth; "Detection of Antigens in Biologically Complex Fluids with Photografted Whole Antibodies", Analytical Chemistry, 2006, 78, pp. 3144-3151.

Kyongmi Chon; Jihee Moon; Suhan Kim; Sang-Don Kim; Jaeweon Cho; "Bio-particle separation using microfluidic porous plus for environmental monitoring", Desalination, 2007, 202, pp. 215-223.

\* cited by examiner

MICROFLUIDIC DEVICES AND METHODS INCLUDING POROUS POLYMER MONOLITHS

STATEMENT REGARDING RESEARCH & DEVELOPMENT

The United States Government has a paid-up license in this invention and the right in limited circumstances to require the patent owner to license others on reasonable terms as provided for by the terms of contract No. DE-AC04-94AL85000 awarded by the U.S. Department of Energy to Sandia Corporation.

TECHNICAL FIELD

Embodiments of the invention relate generally to microfluidic devices, and more specifically to microfluidic devices and methods for making microfluidic devices containing porous monoliths having reactive functional groups.

BACKGROUND

Microfluidic devices may be used in a variety of assays where the capture or modification of target analytes (or substrates) or localized chemical environment affecting target molecules is desired. Generally, microfluidic devices suitable for capturing target analytes may employ biomolecules, antibodies, or other affinity reagents including, but not limited to, DNA probes, RNA probes, aptamers, thioaptamers, antibody fragments, lectins, cell surface receptors, streptavidin and other receptors or ligands immobilized to a surface of the device or a feature within the device. In some devices used for modifying a localized chemical environment a local charge may be modified to facilitate electro-osmotic flow or define a local pH, for example. In other examples, a hydrophobicity or hydrophilicity (e.g., PEG grafting) of a surface may be altered or selected to chemically modify a localized environment.

Accordingly, antibodies may be immobilized to a surface (e.g. electrode, glass, or other two-dimensional surface) of a microfluidic device through an appropriate chemical reaction or treatment. Bulk fluid flow containing the target analyte may then be passed across the treated surface, and target analytes may diffuse down to bind with the antibodies. Subsequent steps are required to detect the bound antigen (e.g. ELISA).

Generally, a multi-step process is used to graft a biomolecule (among others, proteins, antibodies, enzymes, or DNA molecules) to a porous polymer monolith surface. A common approach is to first define a porous polymer monolith framework fabricated with a chemically reactive monomer in the precursor solution (for example glycidyl methacrylate). Biomolecules are subsequently grafted to the surfaces of the porous monolith framework. Biomolecules can be chemically grafted directly to the monolith (for example via amine groups of the biomolecule reacting with the epoxide functionality of a GMA-based monolith). However, intermediate modifications to the monolith framework have been preferred to achieve higher grafting efficiencies. For example, the epoxide functionality of GMA-based monoliths has been modified by i) aminolysis followed by activation with dialdehyde, ii) hydrolysis of epoxide groups followed by oxidation, or iii) hydrolysis of epoxides followed by activation with carbonyldiimidazole before final reaction of these modified functionalities with amine groups of the biomolecule.

Porous polymer monolith frameworks have also been modified or activated in desired regions via photolithography before grafting biomolecules. For example, in a two-step process, a solution containing the photoinitiator benzophenone is loaded into the monolith framework. Upon exposure to UV, the benzophenone molecule abstracts hydrogen from the polymer surface and becomes tethered to the surface only in the UV exposed region or regions. A second solution containing 4,4-dimetheyl-vinylazlactone is loaded into the monolith and tethered to the surface via reaction with the benzophenone. The covalently linked azlactone functionality of the 4,4-dimethyl-vinylazlactone can react with amine groups present on many biomolecules. The net result is that biomolecule immobilization is isolated to the UV activated regions of the monolith that contain the surface grafted benzophenone. Single step processes have also been demonstrated where benzophenone and 4,4-dimetheyl-vinylazlactone are loaded into the monolith and polymerized simultaneously but may polymerize within the pores and clog the monolith.

In another process, the monolith precursor solution may include a photoiniferter species and solid salt particles. After polymerization of the monolith, a porous polymer network structure may be formed by dissolving the salt particles by introducing deionized water. The pores in the monolith are defined by the salt particle size and distribution. An example of this leaching process is described generally in Simms, et. al., "In situ fabrication of macroporous polymer networks within microfluidic devices by living radical photopolymerization and leaching," Lab Chip, 2005, 5, 151-157, which article is incorporated by reference herein in its entirety for any purpose.

DETAILED DESCRIPTION

Figure 1:
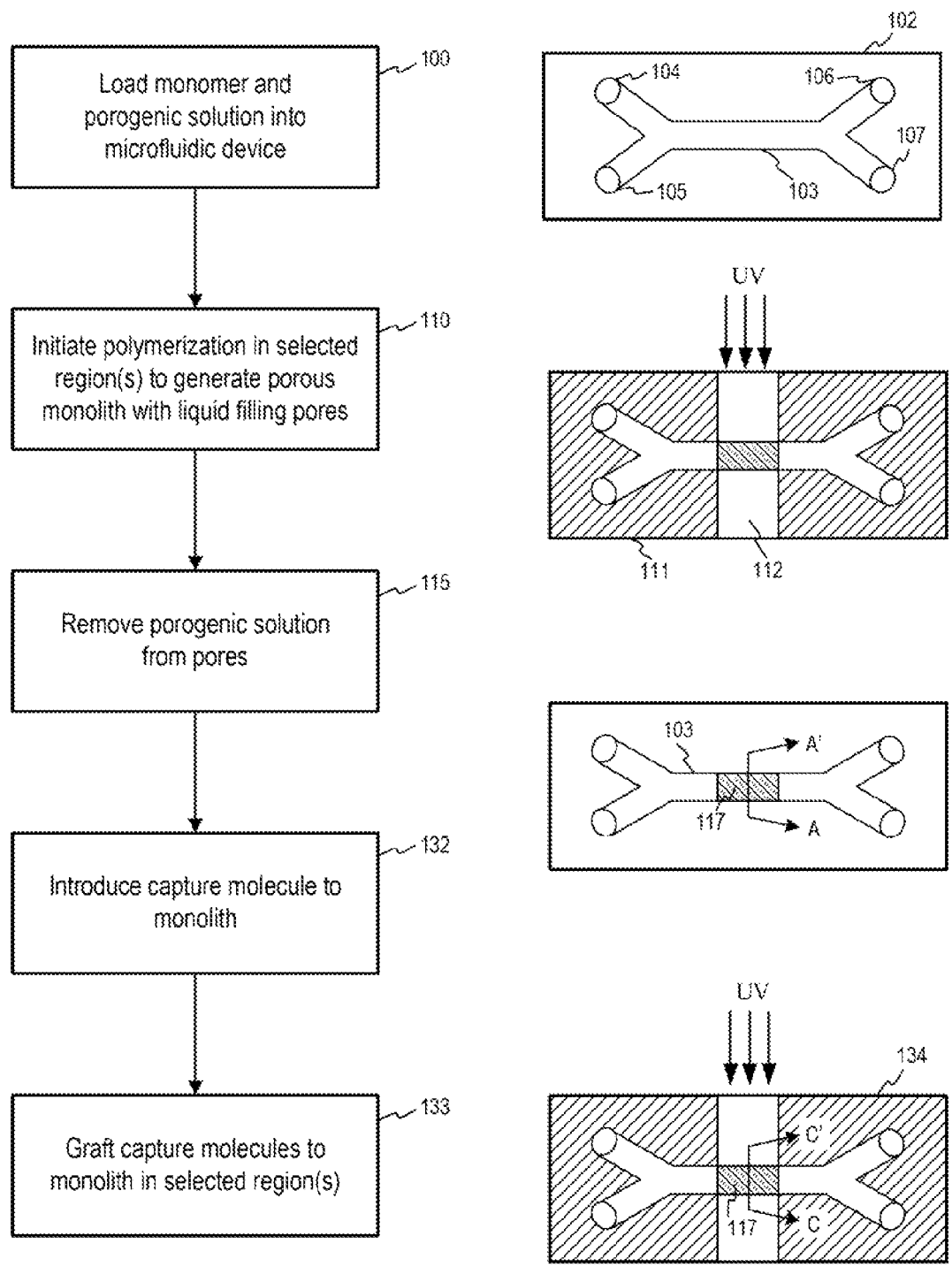
FIG. 1 is a flowchart describing a method for forming a functionalized porous polymer monolith according to an embodiment of the present invention.

Certain details are set forth below to provide a sufficient understanding of embodiments of the invention. However, it will be clear to one skilled in the art that embodiments of the invention may be practiced without one or more of these particular details. In some instances, well-known materials, chemical components, buffers or other additives, analytes, electrical components, material processing and fabrication techniques, have not been shown in detail in order to avoid unnecessarily obscuring the described embodiments of the invention.

Embodiments of the present invention utilize polymerization techniques and include an iniferter species in the monolith precursor solution to yield a porous monolith where pores are defined by a porogenic liquid remaining within the pores. Pore sizes generated utilizing these processes may have a narrower distribution than those generated with a salt leaching technique, described above, which results in a salt contained in the pores.

Iniferter species generally serve as "removable capping groups" on the end of polymer molecules. When the polymer chain containing the removable capping group is exposed again to a suitable energy source, the capping group may be displaced and the polymer chain may provide a reactive site for the binding of a subsequent molecule, such as an antibody or other biomolecule. The amount of biomolecule grafted via this process is a function of exposure time and intensity, the iniferter concentration in the monolith precursor solution, and the initial biomolecule concentration in the graft solution.

Without the inclusion of an iniferter species, the choices for monomer constituents are limited to those that contain appropriate chemical functionality for subsequent biomolecule conjugation (e.g. gylcidal methacrylate, described above, is chosen for its epoxide functional group). The addition of the iniferter species allows chain reactivity to be reinitiated by exposure to UV light or other energy source (via removal of the "capping group") and thus allows more variety in choice of monomer constituents in the monolith precursor solution. For example, monomers can be chosen to tailor mechanical stiffness of the monolith without compromising the chemical reactivity of the monolith. The inclusion of iniferter in the monolith precursor solution may save costly, time-consuming intermediate functionalization and washing steps used for grafting of functional groups, in particular when photo-definition of the grafting is desired. The use of solution-phase porogenic agents rather than salt leaching, such as was described above, may save significant costs and time because the solution phase porogen can immediately be flushed out. Furthermore, the solution-phase porogenic agents may yield tight distributions of pore sizes that can generally be selected over a wide range by adjusting the ratio of porogen to monomer in the monolith precursor solution.

By including an iniferter species in monolith precursor solution, the porous monolith may have surface-exposed reactive chemical groups capable of generating free radicals by introduction of an appropriate energy source of activation energy such as UV light. Appropriately functionalized antibodies, or other biomolecules, may thus be covalently grafted to surfaces of the porous monolith by re-initiating the reactivity of the polymer chains that have been "capped" by the iniferter species. Processes attempting to polymerize or graft biomolecules to a non-reinitiable monolith may polymerize within the pores and clog the monolith.

In this manner, reactive surfaces may be formed on surfaces throughout the polymerized 3-D porous structure. Further, in some examples, the pores of the monolith may be sufficiently large to allow bulk fluid flow through the monolith. Accordingly, sample fluid may be passed through the monolith and target analytes may experience a shorter diffusion distance to a binding site than systems employing bulk fluid flow across a reactive two-dimensional surface. Furthermore, higher density of binding sites may be achieved through the monolith than can be achieved with channel surfaces.

A variety of polymerization techniques may be used to create porous monoliths having pores defined and filled by a liquid porogenic solution. Generally, the polymerization techniques proceed utilizing a liquid solution (monolith precursor solution) having at least two components: a monomer species that will be polymerized into the monolith, and a second solvent (porogen solution) that will define the void pore spaces. Generally, a liquid solution is prepared including the monomer species, crosslinker, initiator, iniferter, and porogenic solution. Monoliths of desired average pore size (and available reactive surface area), and mechanical strength may be created by 1) modifying the ratio of monomer to crosslinker, 2) changing the composition of the porogen solution, and/or 3) modifying the monomer to porogen ratio.

Suspension polymerization, emulsion polymerization, and phase separation polymerization may all be used and differ mainly by the miscibility of the constituents. In suspension polymerization, the monomer and crosslinker may be immiscible with the porogen and the initiator may be soluble in the porogen (e.g. water). Sonication may be required to create uniform dispersed phase. In emulsion polymerization, the monomer and crosslinker may be immiscible with the porogen and the initiator may be insoluble in the porogen medium (e.g. water). Sonication may be required to create uniform dispersed phase, and surfactants may be used. In phase separation polymerization, the monomer and crosslinker and initiator may all be miscible with the porogen. As the polymer is formed, it may then come out of solution. Emulsion polymerization results in particles that may be on the order of 0.05-1 microns in diameter, while phase separation and suspension polymerization may produce polymer particles on the order of 0.1-2 mm.

Relative concentrations of monomer/crosslinker and porogen in the monolith precursor solution are parameters that affect the pore characteristics and mechanical strength of the monolith. In general, for a given monomer/crosslinker density, smaller pores can be achieved by reducing the relative porogen content in the precursor solution.

As will be described further below, iniferter species can be incorporated into mixtures and the above-described polymerization schemes utilized to create porous monoliths containing reactive surfaces that can be reinitiated upon exposure to appropriate energy levels (UV light, heat, etc.). Generally, it has been found that mixtures including an iniferter species may need a longer than anticipated polymerization time to generate a monolith.

FIG. 1 is a flowchart of an example of a method of forming a porous monolith having pores that are defined by a liquid. Generally, as described above, during emulsion, suspension, or phase separation polymerization, polymerized material emerges from a liquid solution. The polymeric portions generally form solid nodules, leaving behind the porogenic solution. The presence of the porogenic liquid phase results in a porous structure, as described further below. Examples of polymerization yielding a porous monolith with liquid in the pores is generally described in U.S. Pat. Nos. 6,782,746 entitled "Mobile monolithic polymer elements for flow control in microfluidic devices," 6,846,399 entitled "Castable three-dimensional stationary phase for electric field-driven applications", and 7,264,723 entitled "Dialysis on microchips using thin porous polymer membranes," each of which is incorporated herein in its entirety for any purpose.

Referring to FIG. 1, in block 100 a liquid solution including the monomer precursor solution may be loaded into a microfluidic device. The liquid monolith precursor solution may generally contain a monomeric solution (composed of a monomeric species and a cross-linking species), an initiator, an iniferter species, and porogenic solution. As will be described further below, the ratios of the components may affect the resulting pore size and strength of the polymerized porous monolith. Microfluidic devices will be described in greater detail below, but a top-down view of a microfluidic device 102 is shown in FIG. 1 including a channel 103 and inlet/outlet ports 104-107. Prior to introducing the monolith precursor solution, all or portions of surfaces of the channel 103 may be treated with silane, or other surface treatments including device materials having been formed with iniferter chemistry, to promote adhesion of the polymer to the channel 103. The monomer portion of the monolith precursor solution may include monomeric species including cross-linker species, an iniferter, and an initiator.

Any of a variety of monomeric species may be used including, but not limited to, mono- and multi-functional acrylates, methacrylates (such as PEGDA, PEDMA, and HEMA (2-hydroxyethyJ methacrylate)), and copolymers and combinations thereof. A variety cross-linking species may he used including, but not limited to multi-functional acrylates and mcthacrylates (such as EGDMA, TEGDMA).

The initiator species serves to generate free radicals on exposure to an energy source (such as heat, chemical reaction, or UV light) and promote polymerization of the monomeric species. Any suitable iniferter may also be used. Suitable iniferters are described, for example, in International Publication Number WO 2004/009489, entitled "Fabrication of 3D photopolymeric devices," which application is hereby incorporated by reference in its entirety. Suitable iniferters are also described in J. Lalevee, et. al. "Controlled Photopolymerization Reactions: The Reactivity of New Photoiniferters," Journal of Polymer Science: Part A: Polymer Chemistry, Vol. 45, 2436-2442 (2007) and T. Otsu, "Iniferter Concept and Living Radical Polymerization," Journal of Polymer Science: Part A: Polymer Chemistry, vol. 38, 2121-2136 (2000), both of which are incorporated herein by reference in their entirety. Generally, and without being bound by the described mechanism, the iniferter species may serve as a reaction initiator, transfer, and terminator. The iniferter is cleaved during the polymerization of the polymer precursor and a portion of the iniferter may be found at the end of the forming polymer. The iniferter may be photoactive, in that once light is removed from the photoiniferter, it caps the surface such that the surface is less reactive. On exposure to light, however, the photoiniferter no longer serves as a cap, and the surface is reactive and able to attach to subsequent material layers. Suitable iniferters include tetraethylthiuram disulfide (TED) and tetramethylthiuram disulfide (TMD). Other iniferters may also be used.

The porogenic portion of the monomer precursor solution may include a variety of solvents, including, but not limited to, water, methanol, and combinations thereof.

The composition of the monolith precursor solution may be selected to achieve phase separation, emulsion, or suspension polymerization and may be selected to achieve a particular maximum, minimum, or average pore size. The ratio of monomer and porogen in the precursor solution (and ratio of monomer to crosslinker within the monomer solution) may be selected to achieve a particular maximum, minimum or average pore size in the polymerized monolith. That is, generally increasing the monomer concentration while decreasing the porogen concentration leads to a decreased pore size in the suspension polymerized monolith Two example recipes for liquid solutions suitable for suspension polymerization are provided below for the purposes of illustration. It is to be understood that the quantities are exemplary only, and other recipes may also be used.

| 10 μm maximum pore size | | |
|---|---|---|
| HEMA | 22% | v/v % |
| EGDMA | 0.8% | |
| Water | 77.2% | |
| DMPA* | 1% | w/v % |
| TED* | 1% | |

| 1 μm maximum pore size | | |
|---|---|---|
| HEMA | 25% | v/v % |
| EGDMA | 18.5% | |
| Water | 28.25% | |
| MeOH | 28.25% | |
| DMPA* | 1% | w/v % |
| TED* | 1% | |

Where HEMA is the monomeric species to be polymerized, EGDMA (ethylene gylcol dimethacrylate) serves as a crosslinker and DMPA the photoinitiator, and TED the photoiniferter. The water and methanol (MeOH) quantities serve as the porogen solution referred to above. The DMPA and TED quantities are given as a weight percentage relative to the HEMA quantity.

An example solution for phase separation polymerization is provided below:

| | |
|---|---|
| Butyl methacrylate | 1.59 mL |
| EGDMA | 0.91 mL |
| MeOH | 4.55 mL |
| DMPA* | 24 mg (1% with respect to the monomers) |
| TED* | 36 mg (1.5% with respect to the monomers) |

Where Butyl methacrylate is the monomeric species to be polymerized, EGDMA is the crosslinker, and MeOH serves as the porogen solution. Utilizing the above phase separation recipe, a polymerization time of 10 minutes at 15 mW/cm$^2$ was used to achieve sufficient polymerization of a porous polymer monolith. This is in contrast to previous recipes that did not incorporate a photoiniferter in which polymerization may have been complete in a shorter time.

The species in the recipes above are combined to yield a final liquid monolith precursor solution, in which all of the components may or may not be miscible. The monomeric species (such as HEMA) may be purchased from a commercially available source and may contain a polymerization inhibitor, such as hydroquinone. Accordingly, the polymerization inhibitor may be removed, for example, by treatment with commercially available beads, prior to polymerizing the solution. The monomeric species may be combined with the photoinitiator, photoiniferter, and porogenic solution in the ratios described above and sonicated to combine. The sonicated solution may then be loaded into a microfluidic device, block 100 in FIG. 1.

Phase separation, emulsion, or suspension polymerization may then be initiated in block 110. The polymerization process may be initiated by exposing selected region(s) to an energy source, such as a UV light source. Regions where a monolith is not desired may be masked from exposure to the light source, as shown in top-down view 111 where region 112 is exposed to a UV light source. In other embodiments, masking may not be necessary if the energy source itself is localized, such as a laser. The exposure duration and energy level may be selected to polymerize the solution. In one example, the exposure may be between 90 and 120 seconds. Regions exposed to the energy source will generally polymerize and appear opaque.

Remaining porogen solution may then be removed in block 115, for example, by drawing the unpolymerized solution through one or more of the inlet/outlet ports 104-107 of the microfluidic device 102. Residual unpolymerized monomer, crosslinker, photoinitiator, and photoiniferter species may also be removed. A porous polymer monolith 117 is accordingly formed in the channel 103.

Figure 2:
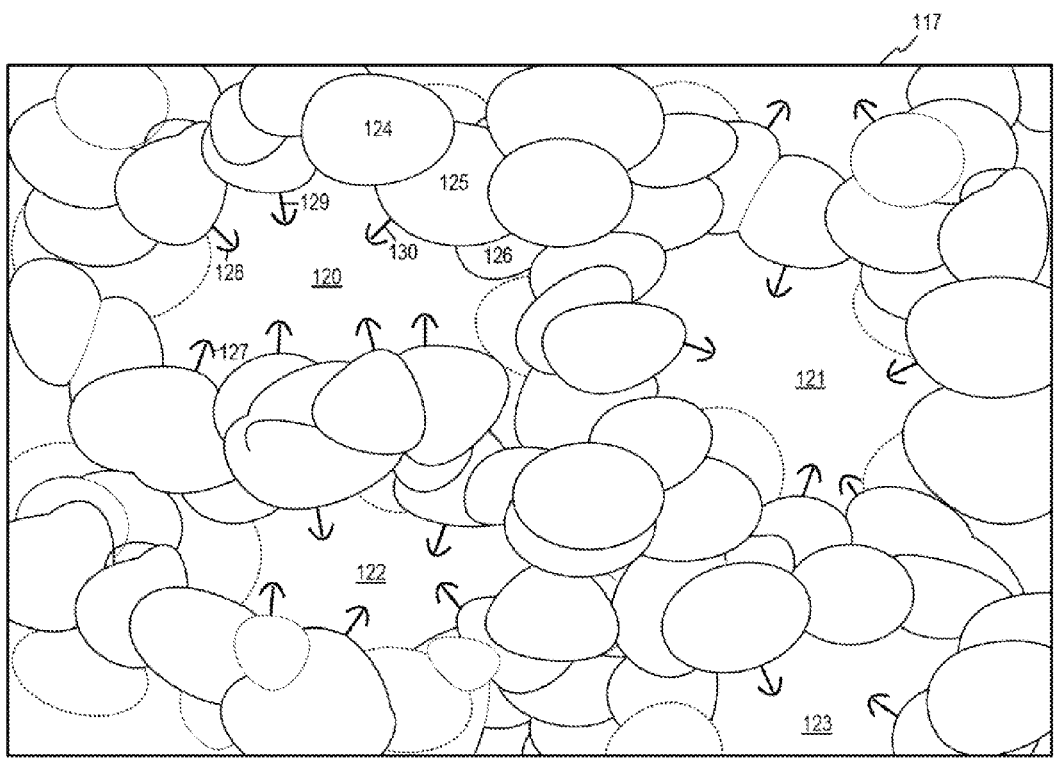
FIG. 2 is a schematic cross-sectional view of a porous polymer monolith according to an embodiment of the present invention.

FIG. 2 is a schematic illustration of a cross-section of the porous polymer monolith 117 along the line A-A' in FIG. 1. Pores 120-123 are shown, defined by polymer nodules including the nodules 124-126. The nodules 124-126 are regions of polymer formed from the monomeric species in the solution. The pores 120-123 correspond generally to regions of the porogenic solution. The pores 120-123 may extend through the length of the monolith 117, and may generally vary in average diameter from about 100 nm-10 μm. The pore diameter may generally correspond to a ratio of monomeric species to liquid phase in the monomer solution. Accordingly, by preparing an appropriate solution, the size of the pores may be controlled. Generally, embodiments of the present invention utilize pore sizes of at least 100 nm to allow bulk fluid flow to occur through the monolith. During the monolith polymerization process, the iniferter species may be cleaved by energy input creating a chain terminating radical such as dithiocarbamyl. An example distinguishing characteristic of polymerization with iniferters is that termination is reversible such that during polymerization of the monolith, the terminating radical is recombined with the propagating radical of the growing polymer chains. After monolith formation, the surfaces may be capped by the reversible chain terminating radical, as illustrated in FIG. 2 by iniferters 127-130 and others. The iniferters 127-130 are illustrated as having a semicircular 'cap' on a reactive surface. The shape is for illustration purposes only, and intended to show that the photoiniferter species may cap the surfaces following polymerization. On subsequent exposure to an energy source, the capping species may reactivate or 'uncap' the polymer chain, yielding free radical sites on the exposed monolith pore surfaces for further polymerization within the monolith pores.

Accordingly, referring back to FIG. 1, the monolith 117 may be functionalized by introducing a biomolecule such as a capture molecule, a functional group, or other species of interest, into the monolith in block 132 and grafting the biomolecule or functional group to the monolith surface. Examples of this process will be further described below with reference to capture molecules; however any of a variety of species may be used. Generally, biomolecules that may be used include nucleic acid sequences, lectins, biotins, ligands, and cell receptors. Functional groups that may be used may include, for example, charged groups, hydrophobic groups, hydrophilic groups, and enzymes. As will be described further below, the species to be grafted may be introduced into the monolith by flowing a solution containing the capture molecules through the monolith. Capture molecules may be grafted to the monolith in block 133 at selected regions by exposing the selected regions to an energy source. Top-down view 134 illustrates an exposure of the entire monolith 117 to a UV light source to graft a capture molecule to the monolith pore surfaces; however, in other examples, only a portion of the monolith may be functionalized. Following removal of unpolymerized material, the monolith may be allowed to swell in water, PBS, or other solution.

Any of a variety of capture molecules may be so grafted, including antibodies or other affinity reagents including, but not limited to, DNA probes, RNA probes, aptamers, thioaptamers, antibody fragments, lectins, cell surface receptors, streptavidin and other receptors or ligands.

Figure 3:
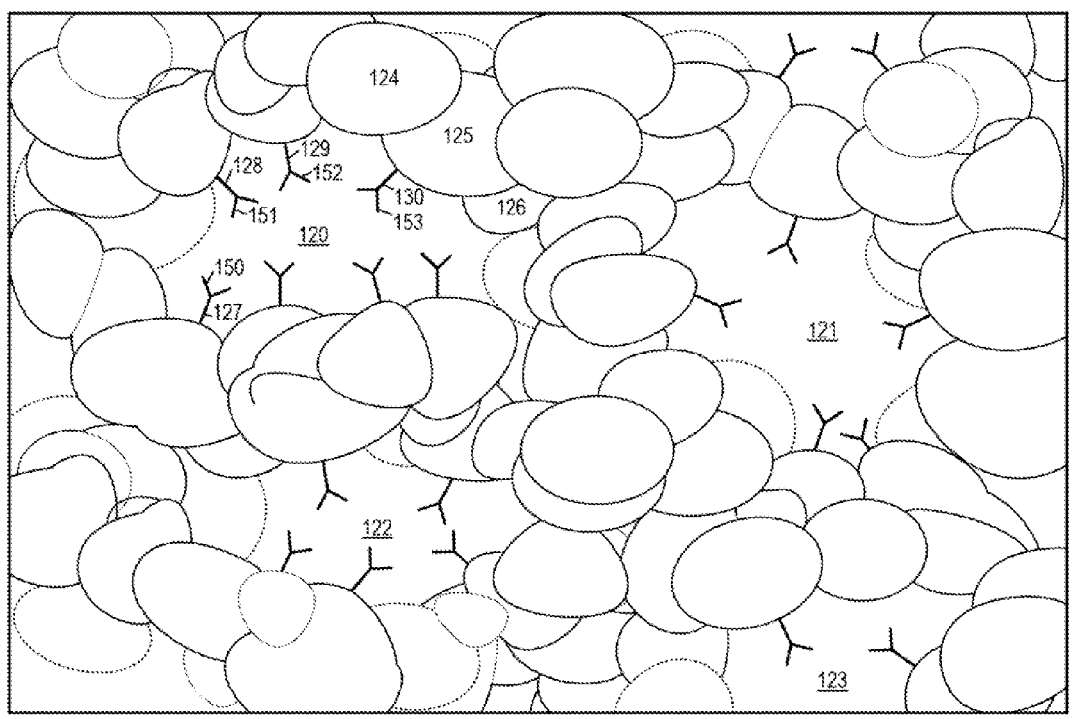
FIG. 3 is a schematic cross-sectional view of a porous polymer monolith according to an embodiment of the present invention.

FIG. 3 is a schematic cross-sectional view of the monolith 117 along line C-C' following grafting of a capture molecule to the surface. As shown, the photoiniferter derived terminating groups 127-130 have 'uncapped', yielding a reactive surface site to which capture molecules 150-153 have bound. In this manner, capture molecules may be bound to pores throughout the three-dimensional region exposed by an energy source.

Referring back to FIG. 1, cell or bead capture may be performed at the monolith 117 by passing a solution containing the cells or beads from, for example, the inlet/outlet port 104 to the inlet/outlet port 107. Beads, cells, or other particles that are larger than the pore size may be concentrated at the monolith 117.

Having described examples of monolith formation above, examples of a microfluidic device incorporating a monolith and capture molecules will now be described, as well as methods for forming and using such a microfluidic device. A microfluidic device typically refers to a device configured to handle fluid having one or more features on the micron or sub-micron scale. That is, a microfluidic device typically has a feature where at least one cross-sectional dimension of the features is between 0.5 μm and 500 μm. Features included in microfluidic devices may include, but are not limited to, channels, chambers, inlet and outlet ports, valves, pumps, electrodes. The microfluidic device may be made utilizing microfabrication techniques including, for example, photolithography, wet and dry etching, and embossing.

Figure 4:
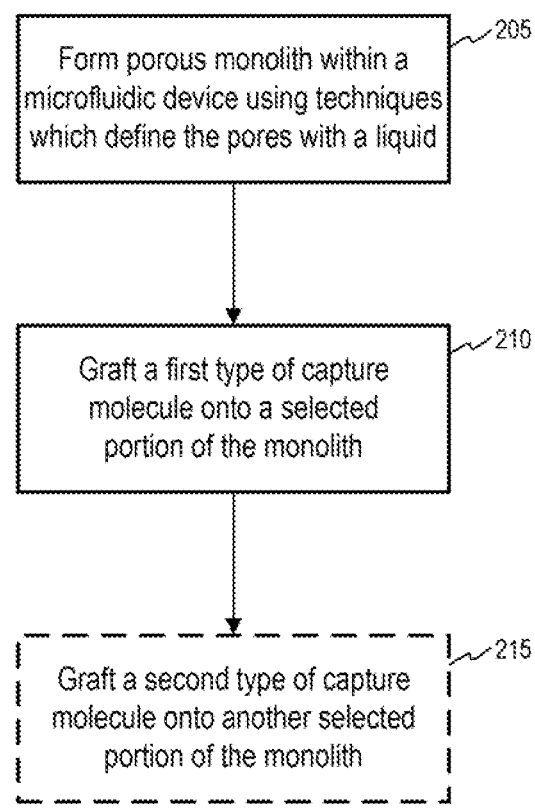
FIG. 4 is a flowchart describing a method for forming functionalized porous polymer monoliths in a microfluidic device according to an embodiment of the present invention.

FIG. 4 is a flowchart illustrating a method of forming different functionalized regions within a monolith in a microfluidic device. At block 205, a monolith is formed within a microfluidic device utilizing polymerization techniques described above. The resulting porous monoliths contain pores defined by a liquid porogenic solution and includes iniferter-derived capping groups bound to pore surfaces. At block 210, a first type of capture molecule is grafted onto a selected portion of the monolith. At block 215, a second type of capture molecule may be grafted onto another selected portion of the monolith. In this manner, any number of different capture molecules may generally be grafted onto selected portions of a monolith.

Referring to block 205, the monolith may be formed within the microfluidic device by introducing an appropriate solution, described above, including an iniferter into a channel or chamber of the microfluidic device. Inlet or outlet ports may be provided for the introduction of the solution, and a pump may be provided on or off of the device to drive flow of the monomer solution into the microfluidic device. Once the solution is in the microfluidic device, polymerization is initiated in desired areas of the microfluidic device by, for example, exposing the desired areas to an energy source. Unpolymerized solution, as well as any remaining porogen may then be removed from the device and a washing step may occur.

Referring to block 210, a first type of capture molecule may be grafted onto a selected portion of the monolith by introducing a fluid containing the capture molecules into the microfluidic device and flowing the fluid through the monolith. The selected portion of the monolith may be exposed to an energy source, such as but not limited to a UV light or a laser. A mask may be used to shield other portions of the monolith from the energy source. The energy source may activate the iniferter-derived capping species in the selected portion of the monolith, generating reactive surfaces to which the capture molecules may bind. In this manner, the capture molecule may be bound to locations throughout the cross-sectional area of the monolith, generally on surfaces of the pores which extend through the monolith.

Referring to block 215, a second type of capture molecule may be grafted onto another selected portion of the monolith by introducing a fluid containing the second type of capture molecules into the microfluidic device and flowing the fluid through the monolith. One or more washing steps may be performed between the blocks 210 and 215. As described above with regard to block 210 and the first type of capture molecule, the second type of capture molecule may similarly be grafted onto a selected region of the monolith by exposing the region to an energy source, activating the iniferter and generating a reactive surface. In this manner, a second type of capture molecule may be bound to locations throughout the cross-sectional area of the monolith.

Accordingly, one or more distinct regions of the monolith may be defined, each having a bound type of capture molecule. The size, location, and shape of the regions may be defined by exposure to an energy source. Accordingly, any number, size, shape, and location of regions may be generated within the monolith in accordance with the number, size, shape, and location of the energy source exposure. A Mixture of capture molecule and other monomers that also react and bind to the activated surface may be introduced for the grafting step. The reaction may proceed in a living radical fashion where a growing polymer chain extends from the initiation sites of the monolith surface. Multiple capture molecules may be grafted in such a fashion and the grafted polymer chain may also incorporate other monomers from a mixture. The incorporation of other monomers, such as spacer monomers, may increase the physical distance of capture molecules with respect to each other and/or the monolith surface. The other monomers may have chemical properties that are different than the monolith surface thereby altering the surface exposed chemical environment in addition to increasing the physical spacing and/or number of capture molecules grafted. PEG acrylate is one example of a spacer group that may be used.

Figure 5:
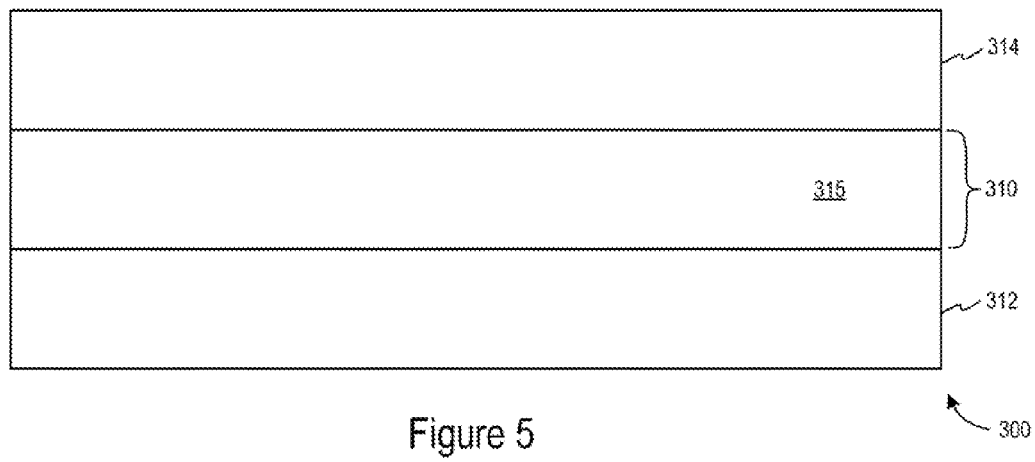
FIG. 5 is a schematic top-down view of a microfluidic device according to an embodiment of the present invention.

FIG. 5 is a schematic top-down illustration of a portion of a microfluidic device 300 according to an embodiment of the present invention. The microfluidic device includes a channel 310 defined in part by walls 312 and 314. The channel 310 is filled with a porous monolith 315, fabricated as described above utilizing a polymerization technique resulting in a porous monolith having pores defined by a porogenic solution and iniferter on the surface of the pores.

The walls 312 and 314 may be made of any of a variety of materials including glass fused silica, PDMS, and plastic, for example. The walls 312 and 314 may be integral with a lower substrate defining a bottom of the channel 310, or may be separate. As described above, the channel 310 may generally be formed by any microfabrication technologies including, for example, embossing, photolithography, and wet and dry etching. The channel 310 generally may range in dimensions of depth from 1 μm to 1 mm, 1 μm to 500 μm in some embodiments, and 10 μm to 300 μm in other embodiments. The width of the channel 310 generally may range from 10 μm to 1 cm, 25 μm to 1 mm in other embodiments, 25 μm to 500 μm in some embodiments, and 25 μm to 150 μm in other embodiments. The dimensions of the channel 310 may be selected according to the ability of the selected techniques and materials to achieve certain dimensions, desired fluid volume, or other parameters. The channel 310 may be covered with a material layer that may or may not be integral with the walls 312 and 314. For example, a glass slide may be used to cover the channel 310. The monolith 315 may be formed in the channel 310 utilizing phase separation polymerization techniques including iniferters as generally described above. As shown, the monolith 315 extends the entire length of the channel 310, but in other embodiments one or more discrete regions of monolith 315 may be formed.

Figure 6:
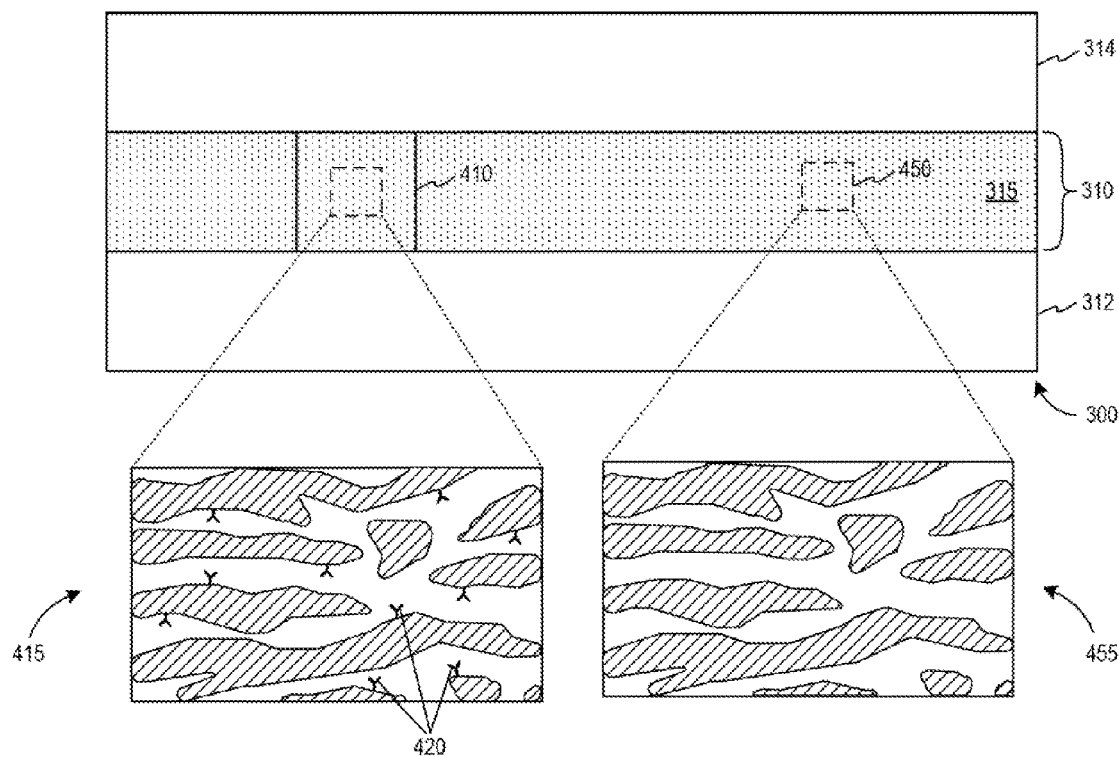
FIG. 6 is a schematic top-down view of a microfluidic device according to an embodiment of the present invention.

FIG. 6 is a top-down schematic illustration of the microfluidic device 300 following grafting of a first capture molecule. As generally described above with reference to FIG. 4, a solution containing a first type of capture molecule may be introduced into the microfluidic device and grafted onto a region of a monolith by exposing the desired region to an energy source, activating the iniferter and creating reactive surface areas throughout a cross-section of the monolith. Referring now to FIG. 5, a region 410 of the monolith 315 is shown having capture molecules bound to the cross-sectional area of the monolith. Again, although capture molecules are shown, other biomolecules, functional groups, or combinations thereof may be grafted to the monolith. An exemplary cross-section 415 is shown, having capture molecules 420 grafted onto surfaces of pores of the monolith. In this manner, capture molecules 420 may be present at pore surfaces throughout the cross-sectional area of the region 410. Other regions of the monolith 315 may not have been exposed to the energy source in the presence of the capture molecules, such as the region 450. Accordingly, capture molecules may not be grafted onto pores of the monolith 315 in the region 450, as shown by the example cross-sectional area 455.

Figure 7:
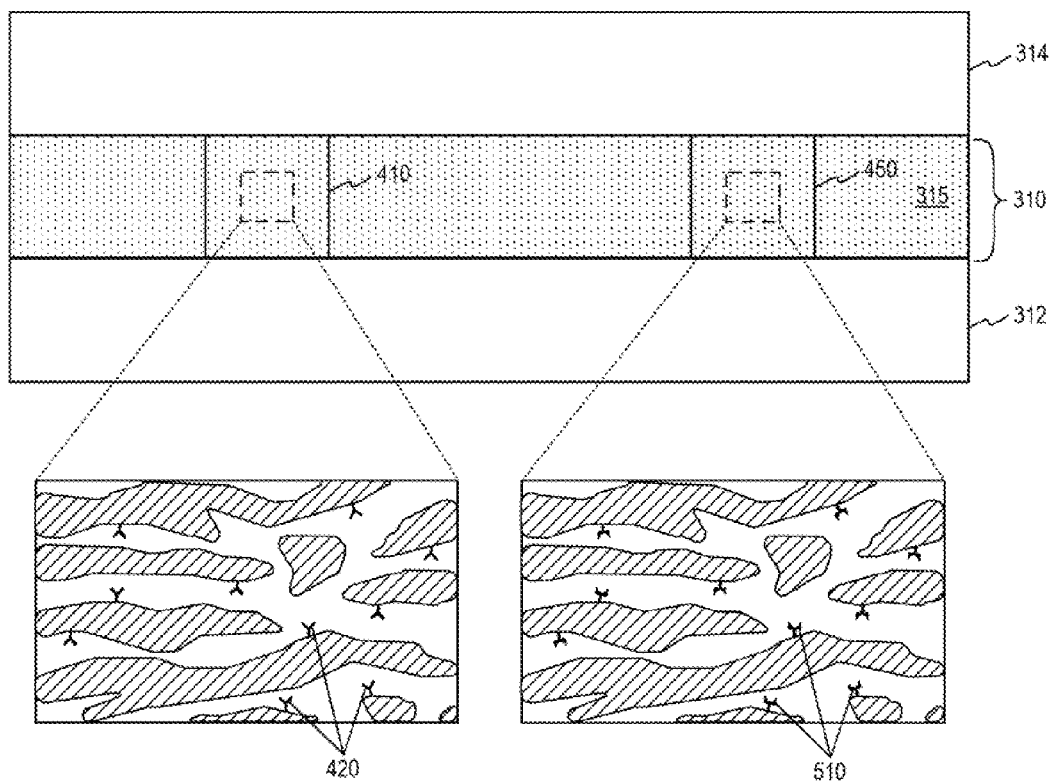
FIG. 7 is a schematic top-down view of a microfluidic device according to an embodiment of the present invention.

FIG. 7 is a schematic illustration of a top-down view of the microfluidic device 300 after grafting of a second type of capture molecule to another region of the monolith. As described above with reference to FIG. 4, a second type of capture molecule may be grafted onto another region of the monolith by washing the monolith, flowing a solution containing the second capture molecule into the monolith, and exposing the region to the energy source, activating the photoiniferters and generating reactive surfaces to which the second type of capture molecule may bind. Accordingly, as shown in FIG. 7 a second type of capture molecule 510 may be bound to surfaces of the pores throughout a cross-sectional region of the monolith 314 in the region 450, as indicated in the cross-sectional view 455 of FIG. 7. Other portions of the monolith 315 may not be exposed to the energy source in the presence of the second capture molecule, so little or no second capture molecule may be bound in the region 410, for example. Two or more different types of capture molecules may be grafted in separate locations of monolithic features that are in fluidic contact with each other if the respective capture molecules are delivered in an isolated fashion to each of the respective monolith regions. For example a device with two or more channels intersecting, crossing through and exiting the main channel through which the respective capture molecules are loaded. The intersecting channels may be spaced from each other at least one intersecting channel width apart and may be spaced several channel widths apart to avoid grafting of more than one capture molecule within the same region of the monolith. The respective monomer solutions may also contain a viscous substance that may be delivered by flow but slows diffusion. Regions of the monolith separating the desired grafting locations may also have patterned hydrophobic surfaces that block transport of hydrophilic monomer solutions from crossing from hydrophilic monomer regions where capture molecules are to be grafted into other regions.

The hydrophilic or hydrophobic regions can be patterned by fabricating a monolith framework and grafting hydrophilic or hydrophobic chemical groups. The grafted chemical groups may also be capped by inclusion of an iniferter in the monomer solution for subsequent modification by grafting.

The different types of capture molecule may be selected to bind with different target analytes, as is indicated schematically in FIG. 7 by the first type of capture molecule 420 having an angular receiving surface and the second type of capture molecule 510 having a rounded receiving surface. These shapes are chosen for illustration purposes only, and actual capture molecules used may bind with corresponding target analytes in different ways—such as chemical or electronic attraction.

Top-down views of a microfluidic device 300 during different stages of the fabrication of discrete regions of capture molecules within a monolith have been shown and described with reference to FIGS. 3-5. Although two regions are shown, generally any number may be included. Further, although the discrete regions have been described as located serially one after another and spaced apart, other configurations are possible, including an array. Note that the porous nature of the monolith 310 allows capture molecules to be photografted throughout a three-dimensional region, including on surfaces of pores extending through the monolith. In this manner, the density of capture molecules may be higher than in devices having capture molecules immobilized only on a two-dimensional surface. Further, as sample with target analyte is drawn through the pores, the target analyte may experience a shorter diffusion distance to the capture molecule than in systems having capture molecules immobilized only on a single surface.

Figure 8:
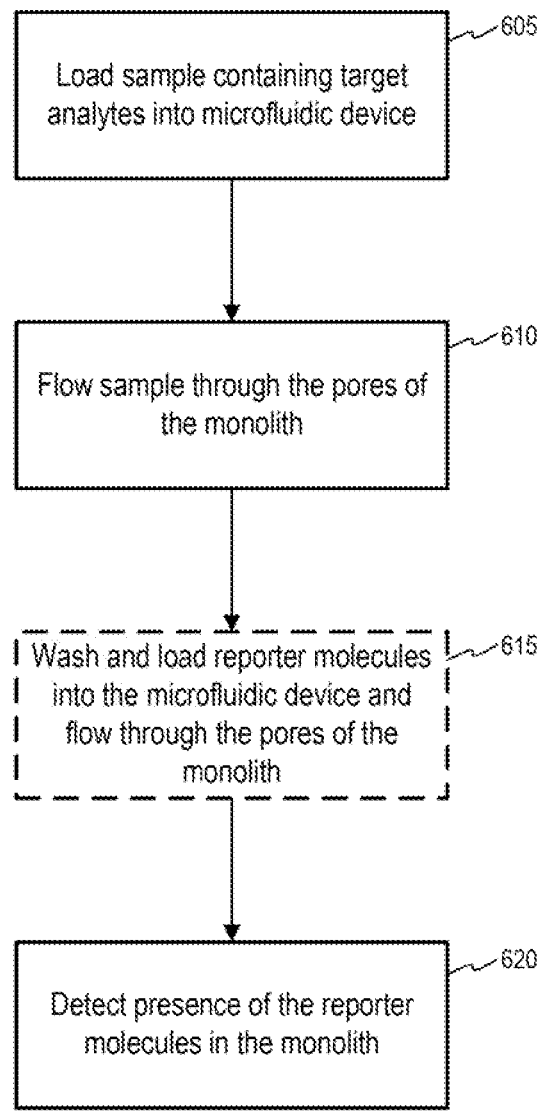
FIG. 8 is a flowchart describing a method of conducting an assay according to an embodiment of the present invention.

FIG. 8 is a flowchart describing a method for performing assay utilizing devices according to embodiments of the present invention. In block 605, a sample containing target analytes may be introduced into a microfluidic device containing porous monoliths with regions of bound capture molecules. In block 610, the sample may be flowed through the pores of the monolith. The target analytes may then diffuse to, and bind to, the relevant capture molecules. In some embodiments, the binding of target analytes to capture molecules may be directly detected, for example, by electrodes positioned to detect the binding or where the target analytes themselves are labeled. However, in other embodiments, further steps may occur to facilitate detection of the bound target analytes. In block 615, the monolith may be washed and reporter molecules may be loaded into the microfluidic device. The reporter molecules are flowed through the pores of the monolith, and may bind to the bound target analytes. In block 620, the presence of the reporter molecules may be detected, providing an indication of the presence of the target analyte.

Referring to block 605, a variety of sample types may be used including biological fluids. The volume of sample fluid needed may be determined in part by the volume of the channel or other features of the microfluidic device.

Referring to block 610, the sample may be flowed through the pores of the monolith utilizing any flow-driving mechanism, including but not limited to pressure driven flow. By passing the sample fluid through the pores of the monolith, target analytes may have a short diffusion distance to the capture molecules.

Referring to block 615, any of a variety of reporter molecules may be used, including but not limited to fluorescent labels, or electronic label molecules. The reporter molecules may generally be selected for their ability to bind to the target molecules, or target/capture molecule complexes. In some examples, the reporter molecules may include enzyme-labeled molecules that may be detected by introducing an enzyme substrate molecule that interacts with the enzyme-labeled molecule to form a detectable reaction product.

Referring to block 620, any number of detection methods may be used, including but not limited to, laser induced fluorescence (LIF), chemiluminescence, or electronic techniques. The detection method may be selected according to the ability to detect the target analyte, target/capture molecule complex, or reporter molecule. For detection, the microfluidic device may be placed into or coupled to a separate detector, or portions of the detection equipment may be integral to the microfluidic device.

Figure 9:
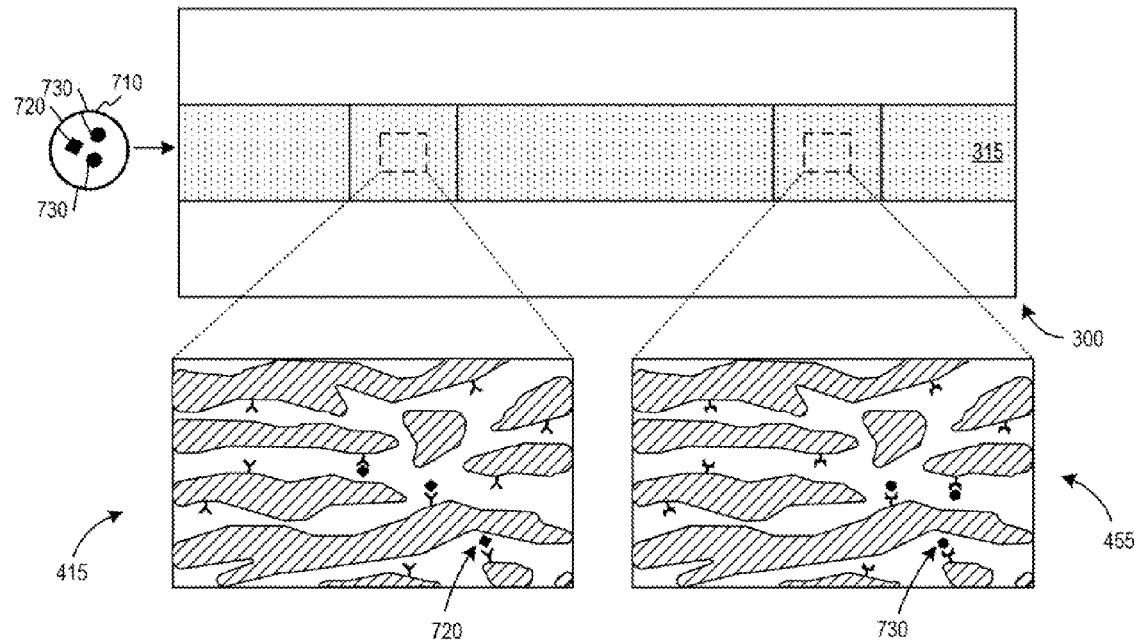
FIG. 9 is a schematic top-down view of a microfluidic device according to an embodiment of the present invention.

FIG. 9 is a schematic illustration of a top-down view of the microfluidic device 300 following introduction of a sample fluid 710. The sample fluid 710 contains two types of target analytes 720 and 730, configured to bind with the capture molecules 510 and 420, respectively. As described above with reference to FIG. 8, the sample 710 may be flowed through the pores of the monolith 315, and the target analytes bound to their corresponding capture molecules, as shown in the cross-sections 415 and 455 in FIG. 9.

Figure 10:
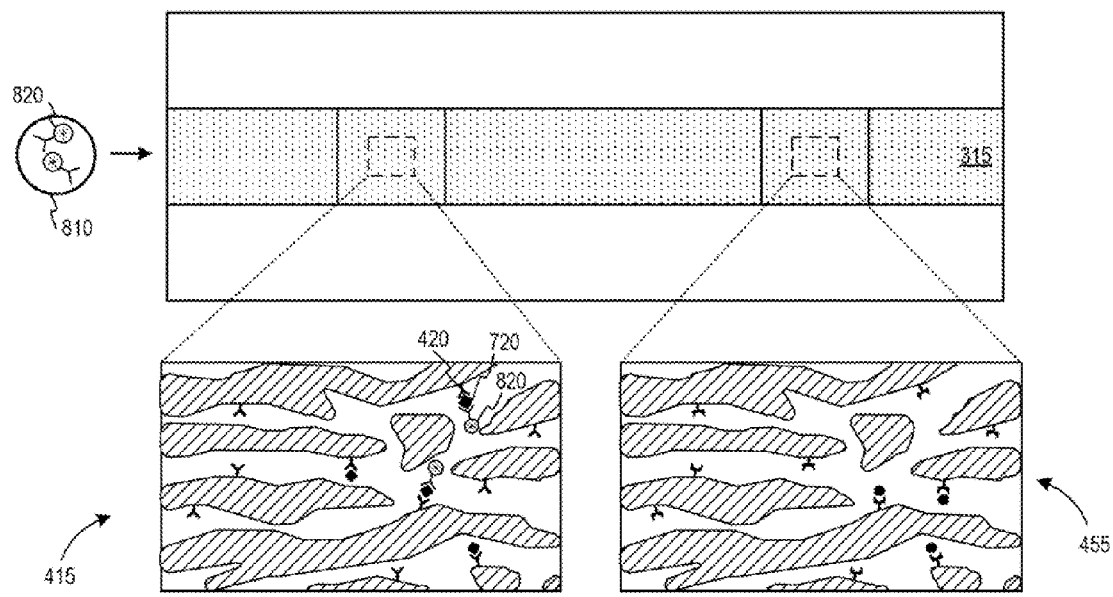
FIG. 10 is a schematic top-down view of a microfluidic device according to an embodiment of the present invention.

FIG. 10 is a schematic illustration of a top-down view of the microfluidic device 300 following introduction of a fluid containing reporter molecules. Herein the fluid 810, comprises reporter molecules 820 that have been selected to bind with the target analyte 720 and capture molecule 420 complexes. As the fluid 810 passes through pores of the monolith 315, the reporter molecules 810 bind to the target analyte 720, or to the target analyte/capture molecule complex. However, the reporter molecules may not bind to the target analyte 730 or target analyte 730/capture molecule 510 complex, as shown in the cross-sections 415 and 455 of FIG. 10. In this manner, the presence, concentration, or both of the target analyte 720 may be identified by detecting the reporter molecule 820. A subsequent fluid may be introduced containing a reporter molecule configured to bind with the target analyte 730 or the target analyte 730/capture molecule 510 complex.

Figure 11:
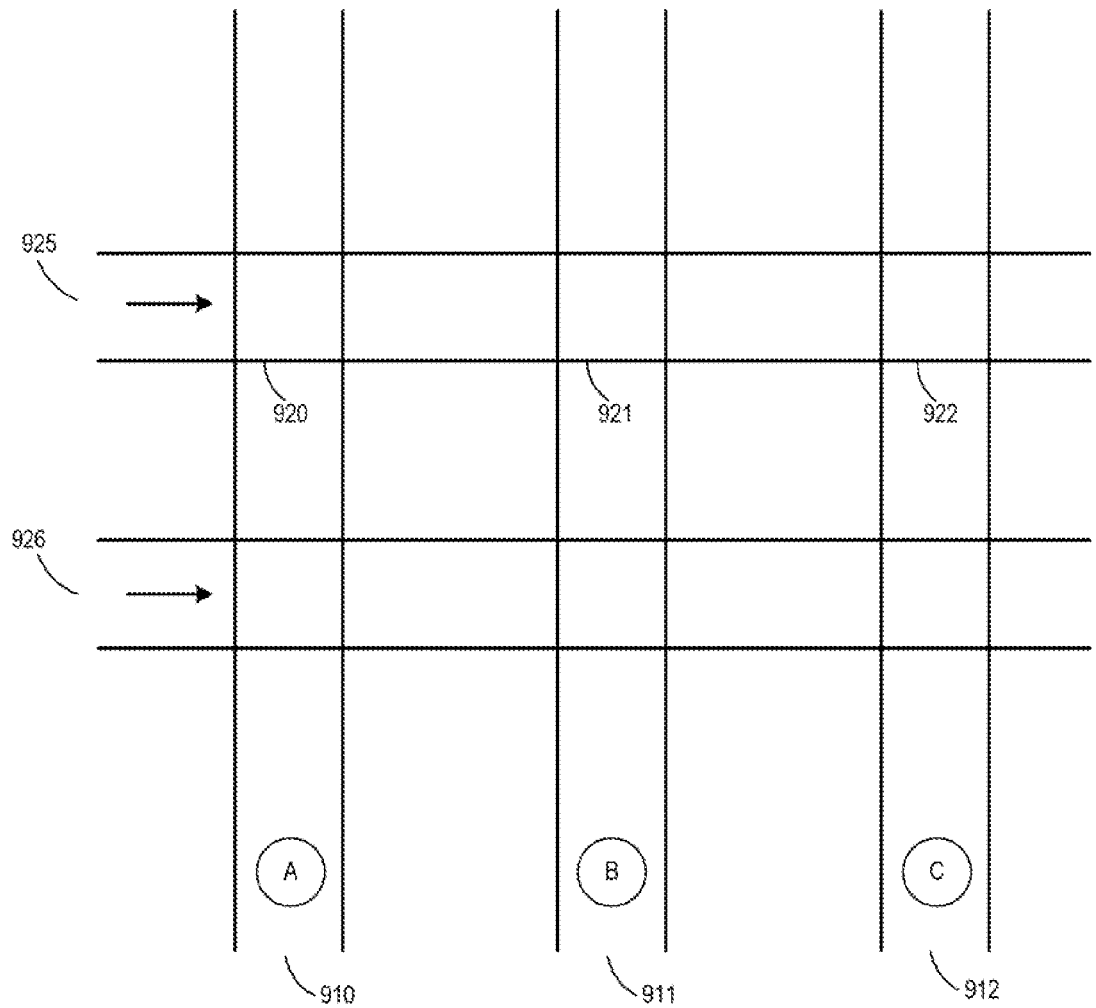
FIG. 11 is a schematic top-down view of a microfluidic device according to an embodiment of the present invention.

A variety of microfluidic device configurations may be used to conduct assays. FIG. 11 is a schematic illustration of a portion of a microfluidic device 900 having intersecting channels. A porous polymer monolith may be formed, as generally described above, in the channels 910-912. Monolith in each of the respective channels may be functionalized using a different capture molecule—molecule 'A' in channel 910, 'B' in channel 911, and 'C' in channel 912. A higher concentration monomer solution may then be loaded into the channels 910-912 and polymerized to form 'walls' at the intersections of the channels, such as the locations 920-922 such that sample fluid may not flow along the channels 910-912. Sample fluid may then be loaded into the cross-channels 925 and 926. The two sample fluids may then pass through the monolith functionalized with the 'A' capture molecule, followed by 'B' and 'C', as indicated. In this manner, numerous sample fluids may be exposed to numerous capture molecules using a device formed in accordance with examples of the invention. Although two sample channels and three capture molecule regions are shown, any number may generally be used.

Devices and methods described herein may find use in a variety of applications. Multi-antibody immunoassays may be performed, as generally described above, to facilitate pathogen or cytokine detection. In other examples, cells may be concentrated at or adhered to a functionalized porous monolith, and stimulated with a stimulating fluid. Various cell secretions, products of cell signaling, or combinations thereof, may then be captured in the porous monolith for detection. In other examples, porous monoliths as described herein may be used for particle separation and downstream analysis, such as but not limited to, blood purification and immunoassays.

From the foregoing it will be appreciated that, although specific embodiments of the invention have been described herein for purposes of illustration, various modifications may be made without deviating from the spirit and scope of the invention.

What is claimed is:

1. A method for forming a functionalized porous polymer monolith, the method comprising:
   loading a liquid monolith precursor solution including a monomer species, a cross-linking-species, an initiator, an iniferter species, and a porogen solution into a microfluidic device;
   polymerizing the liquid solution, including activating the iniferter species, in a region of the microfluidic device to form a porous polymer monolith having pore sizes defined in part by the relative proportions of the constituents in the monolith precursor solution and having the iniferter species present on the surface of at least one pore;
   introducing biological molecules or other functional groups into pores of the monolith; and
   reactivating the iniferter species and grafting at least some of the biological molecules or functional groups onto the surface of at least one pore.

2. The method of claim 1 wherein the monomer species includes an acrylate monomer.

3. The method of claim 1 wherein the monolith precursor solution contains 30-75 percent monomer species by volume.

4. The method of claim 1 wherein the at least one pore has a diameter of between 2 $\mu$m and 50 $\mu$m.

5. The method of claim 1 wherein the porous polymer monolith defines pores in regions corresponding to locations of the liquid porogen solution during monolith formation.

6. The method of claim 1 wherein the introducing, comprises introducing a biomolecule comprising a nucleic acid sequence, lectin, biotin, ligand, a cell receptor, or combinations thereof.

7. The method of claim 1 wherein the introducing comprises introducing a functional group comprising a charged group, a hydrophobic group, a hydrophilic group, an enzyme, or combinations thereof.

8. The method of claim 1 wherein introducing comprises flowing, a solution containing the biomolecule or functional group through the at least one pore.

9. The method of claim 1 wherein polymerization occurs at least in part through emulsion polymerization.

10. The method of claim 1 wherein polymerization occurs at least in part through suspension polymerization.

11. The method of claim 1 wherein polymerization occurs at least in part through phase separation polymerization.

12. A method for forming an array of functionalized monolith regions, the method comprising:
    photopolymerizing a liquid monolith precursor solution including a monomer species, a cross-linker species, a liquid porogenic solution, an initiator, and an iniferter to form a porous polymer monolith having pores defined in part by the liquid porogenic solution and having iniferter on a surface of at least one pore;
    grafting a first type of biological molecule onto a selected portion of the monolith including activating iniferter species within the selected portion; and
    grafting a second type of biological molecule onto another portion of the monolith including activating iniferter species within another portion.

13. The method of claim 12 wherein the monolith precursor solution includes 10-75 percent monomer species by volume.

14. The method of claim 12 wherein the porous polymer includes pores having an average diameter of between 50 nm and 50 $\mu$m.

15. The method of claim 12 further comprising:
    flowing a sample containing target analytes through the porous monolith such that at least some of the target analytes bind to the first type of biomolecule.

16. The method of claim 15 further comprising:
    flowing reporter molecules through the porous monolith to bind with the bound target analyte/biomolecule complex.

17. The method of claim 16 further comprising rinsing the porous monolith with a buffer to remove unbound reporter molecules.

18. The method of claim 16 wherein the reporter molecules comprise fluorescently labeled molecules and the method further includes detecting the reporter molecules including detecting fluorescent emission corresponding to the reporter molecules.

19. The method of claim 16 wherein the reporter molecules comprise enzyme-labeled molecules and the method further includes detecting the reporter molecules including introducing an enzyme substrate that is altered by the enzyme to generate a detectable reaction product.

20. The method of claim 13 wherein the liquid monolith precursor solution is configured for emulsion polymerization.

21. The method of claim 13 wherein the liquid monolith precursor solution is configured for phase separation polymerization.

22. The method of claim 13 wherein liquid monolith precursor solution is configured for suspension polymerization.

* * * * *